United States Patent [19]

Winocur

[11] Patent Number: 4,984,883
[45] Date of Patent: Jan. 15, 1991

[54] TRANSLATION INSENSITIVE KERATOMETER USING MOIRE DEFLECTOMETRY

[76] Inventor: Joseph Winocur, 14 San Ramon, Irvine, Calif. 92715

[21] Appl. No.: 384,159

[22] Filed: Jul. 21, 1989

[51] Int. Cl.$^5$ ............................................... A61B 3/107
[52] U.S. Cl. ................................... 351/212; 351/211; 351/246; 356/35.5
[58] Field of Search ............... 351/211, 212, 209, 210, 351/247; 356/35.5

[56] References Cited

U.S. PATENT DOCUMENTS

| | | | |
|---|---|---|---|
| 4,432,239 | 2/1984 | Bykov | 356/35.5 |
| 4,692,003 | 9/1987 | Adachi et al. | 351/212 |
| 4,850,693 | 7/1989 | Deason et al. | 356/35.5 |

Primary Examiner—Rodney B. Bovernick
Attorney, Agent, or Firm—Roy A. Ekstrand

[57] ABSTRACT

A translation insensitive keratometer includes a pair of laser sources and optical coupling systems for irradiating a specular object. The laser beams are reflected separately back through the optical coupling systems to a pair of moire deflectometers.

5 Claims, 2 Drawing Sheets

TRANSLATION INSENSITIVE KERATOMETER USING MOIRE DEFLECTOMETRY

FIELD OF THE INVENTION

This invention relates generally to the measurement of curved specular objects and particularly to keratometry as applied to the measurement of cornea shape by medical practitioners.

BACKGROUND OF THE INVENTION

In a significant number of medical treatments administered by medical practitioners treating various functions and disorders of the human eye, a need arises to deal with the shape of the outer layer or cornea of the eye. As is known, the cornea is a thin somewhat flexible generally transparent tissue forming the outer coat of the eye which has a nearly spherical curvature. As a result, the human cornea may be regarded approximately as a spherical specular object having negative reflecting power. The latter term refers to the fact that when light is reflected from the cornea its divergence increases. Of particular interest to the present invention, is the need which arises to measure the radius of curvature and topography or shape of the anterior or front service of the cornea. It is often necessary to undertake cornea measurements both statically and dynamically in different diagnoses and treatments. The measurement of cornea surface curvature, shape or topography is referred to as keratometry. To meet the needs of keratometry, various instruments referred to as keratometers have been developed. In most cases, such instruments utilize classical imaging techniques.

Conventional keratometers are limited to measurement only of cornea surface curvature. They cannot map the surface contours of the cornea with high resolution. In addition, they have a slow response time and are unable to measure dynamic changes in surface shape. Finally, they tend to obscure or interfere with the field of view of the examining practitioners or operating surgeons which in turn limits its degree of use.

There arises, therefore, a need in the art for an improved system of keratometry that accurately measures cornea surface topography in real time without interfering significantly with the view of treating surgeons and other practitioners.

The present invention applies moire deflectometry techniques to keratometry. The basic principles of moire deflectometry are illustrated and discussed in detail in a number of publications including an article entitled MOIRE DEFLECTOMETRY: A RAY DEFLECTING APPROACH TO OPTICAL TESTING by Okafri and Iglatt published in OPTICAL ENGINEERING, 24(6), 944–960(Nov./Dec. 1985). As is set forth therein, moire deflectometry utilizes a collimated light beam which is directed toward a parallel pair of optical gratings having alternating equally spaced opaque and clear stripes. The stripes of the two gratings are oriented at a small angular displacement with respect to each other. The interaction of the grating elements and the collimated light beam produce a fringe light pattern on a receiving device such as a screen. As an alternative to a conventional screen, a TV camera utilizing a charge coupled device detector array may be utilized to produce electronic formatted video images.

The basic moire deflectometer described above produces the desired measurement of a lens shape when the light beam incident upon the gratings has been reflected from the to-be-measured object. When so used, the fringe pattern referred to as a moire deflectogram produces a fringe pattern indicative of the shape of the reflecting object. To properly map the two-dimensional shape of an object, two measurements are required in which the reflected light from the object is passed through grating pairs which are rotated ninety degrees between measurements. In most of the moire deflectometers presently utilized for optical measurements, the collimated light beam is usually provided by a helium neon laser having a wavelength of approximately six hundred thirty three nanometers.

While the foregoing described conventional moire deflectometers have achieved some level of success for use in optical testing, their use for keratometry would be subject to several problems and limitations. One of the most significant limitations arises from the dependence of the system's accuracy upon the careful placement or measurement of the distance between the deflectometer and the cornea surface. That is to say, the measurement made is extremely sensitive to this distance and careful calibration must be utilized. In addition, great difficulty is experienced in maintaining a static position of the human eye being examined which further exacerbates the problem.

SUMMARY OF THE INVENTION

Accordingly, it is a general object of the present invention to provide an improved keratometer. It is a more particular object of the present invention to provide a translation insensitive keratometer using moire deflectometry. It is a still more particular object of the present invention to provide an improved translation insensitive keratometer using moire deflectometry which provides measurement of cornea surface topography dynamically and in real time and which permits simultaneous viewing of the measured object by practitioners.

In accordance with the present invention, there is provided a translation insensitive kertometer having a pair of separate light beams of different radii of curvature for focusing upon a to-be-measured object. A pair of moire deflectometers are coupled to and receive the reflected light from each of the light sources. Each moire deflectometer is provided with a video camera receiving device and appropriate image processing circuitry.

The features of the present invention, which are believed to be novel, are set forth with particularity in the appended claims.

The invention, together with further objects and advantages thereof, may best be understood by reference to the following description taken in conjunction with the accompanying drawings, in the several figures of which like reference numerals identify like elements and in which.

DESCRIPTION OF THE PREFERRED EMBODIMENT

Figure 1:
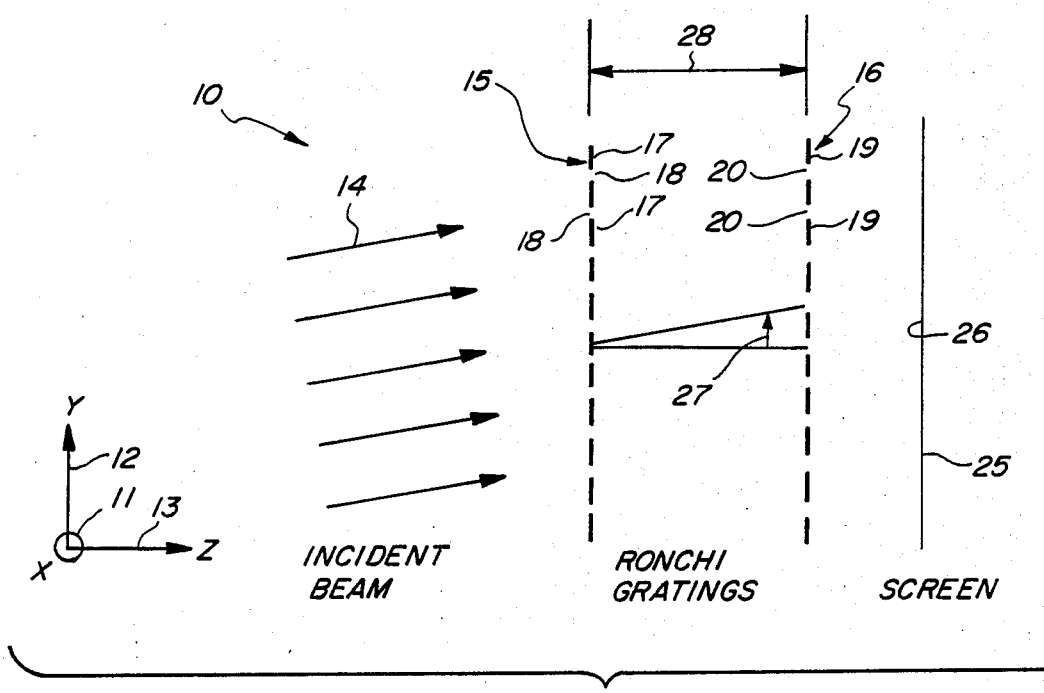
FIG. 1 is a schematic diagram of a basic moire deflectometer imaging a phase object.

FIG. 1 sets forth a typical moire deflectometer imaging a phase object (not shown) generally referenced by numeral 10. A pair of deflection grating members 15 and 16 are supported in a spaced arrangement such that gratings 15 and 16 are generally parallel and spaced by a predetermined distance 28. A screen 25 having a suitable light reflecting surface 26 is supported on one side of grating 16 and is generally parallel thereto. Grating 15 comprises a plurality of parallel opaque strips or elements 17 separated by an equal plurality of light transmissive strips 18. Similarly, grating 16 comprises a plurality of parallel equally spaced opaque elements 19 separated by a plurality of parallel equally spaced transparent elements 20. Grating 15 is oriented such that the elements thereof are parallel to X-axis 11 and are perpendicular to Y-axis 12 and Z-axis 13. In addition, grating 16 is positioned such that its opaque elements 19 are oriented at a small angle with respect to the opaque elements 17 of grating 16. A collimated light beam 14 is directed to gratings 15 and 16 and is incident thereon at a small angle 27. Collimated light beam 14, therefore, passes through gratings 15 and 16 and impinges surface 26 of screen 25. In accordance with the well known moire effect, the light pattern produced at surface 26 of screen 25 is a fringe pattern generally referred to as a moire deflectogram. In accordance with general principles of moire deflectometry, the fringe pattern on surface 26 of screen 25 provides an indication of the character of the phase object through which light beam 14 was originally transmitted.

Figure 2:
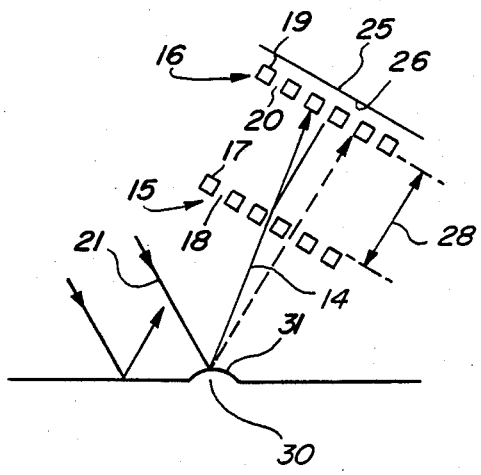
FIG. 2 is a schematic diagram of a moire deflectometer imaging a specular object.

FIG. 2 sets forth a schematic diagram of a typical moire deflectometer in measurement of a specular object. Accordingly, a pair of gratings 15 and 16 described above in FIG. 1 include parallel opaque elements 17 and 19 respectively separated by parallel transparent elements 18 and 20. As described above, gratings 15 and 16 are separated by a distance 28. A screen 25 is positioned generally parallel to grating 16 and defines an image surface 26. A collimated light beam 21 is directed at a to-be-measured specular object 30 which defines a reflective surface 31, the contour of which is to be measured by the moire deflectometer. In accordance with the reflection characteristic of surface 31, collimated beam 21 is reflected therefrom in the form of a light beam 14 which passes through gratings 15 and 16 to produce a moire deflectogram on screen surface 26.

FIGS. 1 and 2 taken together set forth the basic principles of moire deflectometry as presently utilized in the art. It will be apparent to those skilled in the art that a number of variations of the moire deflectometer structures described in FIGS. 1 and 2 have been constructed and have been used. It is less well known, however, that the present structures, particularly when applied to keratometry, are subject to the above-described shortcomings and limitations toward which the present invention is directed.

Figure 3:
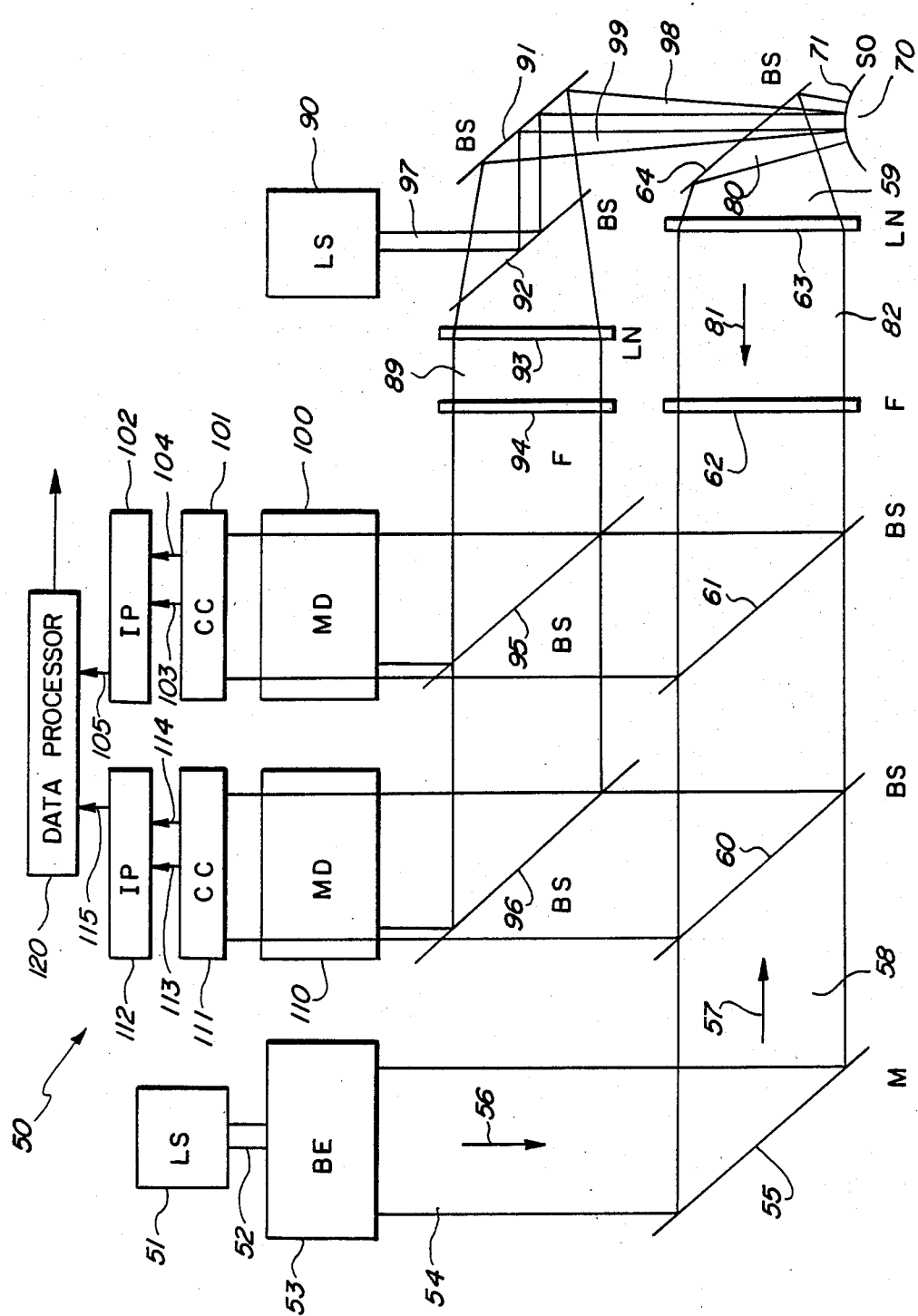
FIG. 3 is a schematic diagram of the present invention translation insensitive keratometer using moire deflectometry.

FIG. 3 sets forth a translation insensitive keratometer using moire deflectometry constructed in accordance with the present invention and generally referenced by numeral 50. Keratometer 50 includes a laser 51 and a beam expander 53. Laser 51 produces a single wavelength light beam 52 which is expanded by beam expander 53 to form an expanded beam 54. Beam expander 53 is directed toward an angled mirror 55 which reflects expanded beam 54 to a reflected beam 58 directed in the direction indicated by arrow 57. A pair of angled beam splitters 60 and 61 are positioned within the path of reflected beam 58 such that beam 58 passes through beam splitters 60 and 61. A filter 62 having a predetermined filter characteristic is positioned within the path of light beam 58 downstream of beam splitters 60 and 61. A converging lens 63 is positioned in the path of reflected beam 58 downstream of filter 62 and converges beam 58 to a converging light beam 59. A beam splitter 64 is positioned in the path of converging light beam 59 and reflects light beam 59 as reflected beam 80. A specular object 70 having a reflective surface 71 is positioned within the path of reflected beam 80.

A moire deflectometer 100, constructed in accordance with conventional moire deflectometry construction and a charge coupled device TV camera 101, are optically coupled such that the output of moire deflectometer 100 is imaged by camera 101. An image processing system 102 is coupled to camera 101. A second moire deflectometer 110 and a second charged coupled device TV camera 111 are coupled such that camera 111 images the output of moire deflectometer 110. An image processing system 112 is coupled to camera 111. A pair of beam splitters 95 and 96 are positioned beneath moire deflectometers 100 and 110 respectively and in general alignment. A transmission filter 94 having a predetermined filter characteristic is aligned with beam splitters 95 and 96. A converging lens 93 is positioned in alignment with filter 94. A laser 90 producing a collimated beam of light 97 having a predetermined wavelength different from light beam 52 of laser 51 and a pair of beam splitters 92 and 91 cooperate to direct light beam 97 to surface 71 of specular object 70.

In operation, light beam 52 produced by laser 51 is expanded by beam expander 53 to form expanded beam 54 which travels in the direction indicated by arrow 56 to impinge mirror 55. Beam 54 is reflected from mirror 55 to form a reflected light beam 58 travelling in the direction indicated by arrow 57. Beam 58 passes through beam splitters 60 and 61 and is filtered by transmission filter 62. Thereafter, beam 58 is converged by lens 63 to form a converging beam 59 which is reflected by beam splitter 64 to impinge surface 71 of specular object 70. The spherical character of surface 71 imparts a divergent character to reflected beam 80 which is partially reflected by beam splitter 64 back through lens 63. Lens 63 collimates reflected beam 80 to form a collimated reflected beam 82 travelling in the direction indicated by arrow 81. Reflected beam 82 passes through filter 62 and is partially reflected by beam splitter 61 passing through 95 to be received and analyzed by moire deflectometer 100. Moire deflectometer 100 in turn produces a moire deflectogram which is received by camera 101 and processed by image processing system 102. The portion of reflected beam 82 transmitted through beam splitter 61 is reflected by beam splitter 60 and transmitted through beam splitter 96 to impinge moire deflectometer 110. Moire deflectometer 110 in turn produces a moire deflectogram which is imaged by camera 111 to produce an image signal which is processed by image processor 112. It should be noted that in accordance with an important aspect of the present invention the grating screens of moire deflectometer 110 are oriented orthogonal to those of moire deflectometer 100. As a result, the deflectograms produced by moire deflectometers 100 and 110 in processing reflected beam 82 simultaneously produce the orthogonally related moire deflectograms required for dynamic testing and measurement.

Laser 90 produces a small collimated light beam 97 which is partially reflected by beam splitter 92 to impinge beam splitter 91 and be partially reflected therefrom once again as reflected beam 98 which passes through beam splitter 64 to impinge surface 71 of specular object 70. Beam 98 is reflected from spherical surface 71 of object 70 as a divergent beam 99 which passes through beam splitter 64 and is reflected from beam splitter 91 and thereafter transmitted through beam splitter 92. The divergent beam passing through beam splitter 92 is collimated by lens 93 to form a collimated beam 89 which passes through transmission filter 94 and is partially reflected by beam splitter 95 to impinge moire deflectometer 100. The portion of beam 89 passing through beam splitter 95 is partially reflected by beam splitter 96 to impinge moire deflectometer 110. The images produced by moire deflectometers 100 and 110 in response to beam 89 are received by cameras 101 and 111 respectively and converted to electronic signals which are processed by image processors 102 and 112.

It should be noted that filter 62 has a filter characteristic permitting transmission of the wavelength of light produced by laser 51 but preventing transmission of the wavelength of light produced by laser 90. Conversely, the filter characteristics of filter 94 are selected to provide transmission of the output light of laser 90 while preventing transmission of the output light produced by laser 51. The wavelengths of light produced by lasers 51 and 90 are chosen to correspond to two different primary colors of cameras 101 and 102 such as blue and red, blue and green, or green and red. The charge coupled device color TV cameras 101 and 111 produce different signals for each primary color received which are then processed by image processors 102 and 112 respectively. Thus, the output signals of cameras 101 and 111 comprise separate moire deflectograms for moire deflectometers 100 and 110 respectively for each of the light signals processed from lasers 51 and 90.

Equations 1 through 25 are discussed and set forth below and are referred to at this point to aid the reader's understanding. The output signals of camera 101 are labeled 103 and 104, corresponding to the deflectograms produced by moire deflectometer 100 from laser sources 51 and 90, respectively. The image processor 102 measures the angular rotation of the moire fringe pattern in each deflectogram caused by variation of y-curvature and/or position of surface 71 of the specular object 70. In dynamic operation, the change in y-radius δay and the change in displacement δz are calculated according to Equations (22), (23), (24) and (25) are set forth below for the measurement of y-radius of curvature. The measurement of δz is redundant. This fact can be used to derive an improved algorithm to calculate δax, δay, and δz.

Data processor 120 computes the topography of the specular object according to Equations (3) and (4), and (16). The outputs of data processor 120 are the position, x-curvature, y-curvature, and a numerical map of the topography of the surface 71 of the specular object 70.

It should be noted that beam 52 of laser 51 is injected into the optical system at a point upstream of lens 63 while beam 97 of laser 90 is injected into the optical system at a point downstream from lens 93. As a result and in accordance with an important aspect of the present invention, beam 52 from laser 51 is focused by lens 63 to a point at a distance beyond surface 71 of object 70 which is equal to the radius of curvature of object 70. Since beam 59 is focused at the center of curvature of surface 71 of object 70, beam 59 is reflected normal to surface 71 of object 70. The incident and reflecting beams therefore are reciprocal, meaning that they have identical magnitudes of radius of curvature but are opposite in sign. As a result, the radii of the incident beam and reflected beam upon surface 71 are identical and both equal to infinity at the entrances to moire deflectometers 100 and 110. As a result, the curvature of both the transmitted and received beams can be measured simultaneously by a single pair of moire deflectometers. This represents a substantial departure from the conventional configuration set forth above in which the incident and reflected light beams do not share a common transmission path and are not reciprocal.

It should be noted that the only elements placed above object 70 are beam splitters 64 and 91 which in accordance with their partially transmitting characteristics permit the surgeon or other medical practitioner to have direct visual and laser beam access to object 70 (the cornea). It should be noted that beam splitters 64 and 91 may be fabricated to be transparent in the visible wavelengths of light for radial keratotomy surgery and/or transparent in the ultraviolet wavelength for laser ablation surgery and/or transparent in the infrared wavelengths for thermal keratoplasty surgery.

The described inventive system is better understood with reference to the following material. To map the two dimensional local variation of wavefront direction, two measurements are required. In the first measurement, the rulings are parallel to the x-axis and the measured angular deflection, $\phi_y$, is in the direction y. In the second measurement, the rulings are parallel to the y-axis and the measured angular deflection, $\phi_x$, is in the direction x. The two measurements can be performed with a single moire deflectometer by rotating the grating pair by ninety degrees between measurements, or they can be performed with the use of two moire deflectometers. Dynamic wavefront measurements require the use of two moire deflectometers.

The basic equations relating the local angular direction $\phi_y(x,y)$, $\phi_x(x,y)$ of an incident light beam to the measured fringe displacements X and Y are $$\tan[\phi_y(x,y)] = X(x,y)\theta/d \quad (1)$$

$$\tan[\phi_x(x,y)] = Y(x,y)\theta/d \quad (2)$$

where $\theta$ is the angle between rulings of the two gratings (generally Ronchi gratings), and d is their separation. The angle $\theta$, and the separation, d, are assumed to be the same for both measurements. For small values of angular deflection, the fringe displacements are perpendicular to the direction of the rulings. The local variations of angular deflection of an incident light beam produced by a specular object such as the anterior surface of the cornea are related to the shape (height function) h(x,y) of the surface of the cornea by the self consistent solutions to the redundant equations $$h(x,y) = k \int \phi_y(x,y) dy \quad (3)$$

$$h(x,y) = k \int \phi_x(x,y) dx \quad (4)$$

where k is a geometric constant related to the distance between the front surface of the cornea and the moire deflectometer. If the probe light beam incident on the cornea is not collimated, then k also depends upon the wavefront curvature of the incident light beam.

The conventional approach to using moire deflectometry to measure the shape of a specular object is illustrated in FIG. 2. A collimated light beam, usually provided by a HeNe laser of a few mW (wavelength=633 nm) is incident on the specular test object. The beam reflected from the specular surface is analyzed by a moire deflectometer. The effect of a specular test object of focal length f on a moire deflectogram is a rotation of the fringes about the len's center. The rotation angle $\alpha$ for small values of $\theta$ is given by $$\tan \alpha = d/f\theta \tag{5}$$

If the moire deflectometer is located a distance l from the specular test object, then the rotation angle is given by $$\tan \alpha = d/R\theta \tag{6}$$

where $$R = f + l \tag{7}$$

is the radius of curvature of the light beam incident on the moire deflectometer.

For a spherical specular test object, the focal length of the test object by the equation $$f = a/2 \tag{8}$$

Therefore, the radius of curvature of the specular test object is given by $$a = 2(R - l) \tag{9}$$

where R is the wavefront radius measured by the moire deflectometer. This equation shows that the distance L must be measured with very high precision in order for the calculated value of the radius a to be very accurate.

The proposed invention circumvents the need to measure L, by using two different light beams of differing radius of curvature. The measurement geometry is designed so the difference between measured radii of curvature of the two beams reflected from the specular test object gives a direct measure of radius a that is independent of the distance l.

Suppose now that a lens such as lens 63 or lens 93 of FIG. 3 intercepts the light reflected from the test object. Then it is easy to show by elementary optical analysis that the radius of the reflected beam at the lens is given by the general equation $$R = L + ab/(2b - a) \tag{10}$$

where L is the distance from the front surface of the specular object to the lens, and b is the focal point of the lens measured with respect to the front surface of the specular object. For the beam from laser 51, $b = \infty$, and for the beam from laser 90, $b = a$. Therefore, $$R1 = L1 + a \tag{11}$$

$$R2 = L2 + a/2 \tag{12}$$

where R1 is the radius of the beam from laser 51 at lens 63, R2 is the radius of the beam from laser 90 at lens 93, L1 is the distance of lens 63 from the front surface of the specular object, and L2 is the distance of lens 93 from the front surface of the specular object. A calibration procedure, described in the next section is used to measure R1, R2, and $$\delta L = L2 - L1 \tag{13}$$

Then a is calculated from the equation $$a = 2(R1 - R2 + \delta L) \tag{14}$$

The calculated value of a is insensitive to the position of the specular object. The constant k in Equations (3) and (4) is calculated from $$k = L/a + b/(2b - a) \tag{15}$$

Since only the beam from laser 51 is used to measure the topography of the specular test object, it follows that $$k = L1/a + 1 \tag{16}$$

As to calibration, the purpose of the calibration procedure is to determine the values of R1, R2 and $\delta L$ in Equation (14) so that the radius of the specular test object can be measured, and to determine the value of k in Equations (3) and (4) so that the topography of the specular object can be measured. The calibration procedure is performed when the instrument is assembled and periodically thereafter, to be certain that the calibration constants are correct. The calibration procedure is relatively straightforward and can easily be performed manually by the operator or it can be automated. The procedure is as follows:

1. Procure a standard spherical specular object with very accurately known radius of curvature that is nearly equal to the radius of curvature of the specular test object. Place the standard spherical specular object in the test position shown in FIG. 3. The precise location of the test position is not important, because the calibration procedure is insensitive to the precise location of the standard specular object.

2. Lens 63 with focal length f1 approximately equal to R1 at its nominal position is mounted on a precise translation stage with position readout. Adjust the position of lens 63 by moving the translation stage until the fringe rotation angle measured by moire deflectometer 100 is zero. This signifies that the reflected beam is collimated at the entrance to moire deflectometer 100. In this position, R1=f1. Since the standard reflecting object is spherical in shape, the fringe rotation angle measured by moire deflectometer 110 will also be zero.

3. Lens 93 with focal length f2 approximately equal to R2 at its nominal position is mounted on another precise translation stage with position readout. Adjust the position of lens 93 by moving the translation stage until the fringe rotation angles measured by moire deflectometers 100 and 110 are zero. In this position, R2=f2.

4. Calculate $\delta L$ from the measured values of R1, R2, and the known value of the radius, a, of the standard specular object, according to Equation (14). Calculate the constant k in Equations (3) and (4), from Equation (16).

Using a programmable motion control system, which is available from a number of different suppliers, the entire calibration procedure can be automated. The operator would simply place the standard specular object in position, and press the calibration button.

Static operation means that the position and radius of curvature of the specular test object do not change in time. In this case the test procedure is identical with the calibration procedure, with the exception that the specular test object is placed in the sample holder instead of the standard specular object. The image processor analyses the test data and calculates the radius of curvature of the specular test object from Equation (14), and calculates the surface topography from Equations (3) and (4), using the parameter values calculated in the calibration procedure.

In dynamic operation, the y-radius of curvature, $\delta ay$, the radius of curvature, $\delta ax$ and the position z of the specular test object may change in time. If the symbol $\delta a$ is used to represent either $\delta ax$ or $\delta ay$ as appropriate and $\delta z$ is the displacement of the specular test object, then it can be shown by elementary optical analysis that the radius of curvature of the reflected beam changes by $$\delta R = -2\delta a/(a/b-2)^2 + \delta z[1+1/(1-2b/a)^2] \quad (17)$$

and the topographic constant k changes by $$\delta k = \delta R/a \quad (18)$$

For the two cases of interest here, $$b = a: \delta R1 = -2\delta a + 2\delta z \quad (19)$$

$$\delta k = -2\delta a/a + 2\delta z/a \quad (20)$$

$$b = \infty: \delta R2 = -\delta a/2 + \delta z \quad (21)$$

The changes in radii of curvature $\delta R1$ and $\delta R2$ are detected as a rotation of the fringe pattern in moire deflectometer 100 or 110. From Equation (6), it follows that a change in radius $\delta R1$ produces a rotation of the fringe pattern by an angle $\delta\alpha 1$, which for small values of $\delta\alpha 1$ is given by $$\delta\alpha 1 = -(d/\theta R1^2)\delta R1 \quad (22)$$

A similar equation applies to $\delta R2$ and $\delta\alpha 2$, $$\delta\alpha 2 = -(d/\theta R2^2)\delta R2 \quad (23)$$

The change in radius, $\delta a$, and the displacement, $\delta z$, are calculated from the measured changes in radius, $\delta R1$ and $\delta R2$, by means of the equations $$\delta a = 2\delta R2 - \delta R1 \quad (24)$$

$$\delta z = (4\delta R2 - \delta R1)/2 \quad (25)$$

which are easily derived from Equations (19) and (21). The image/data processor can easily be programmed to calculate $\delta a$ and $\delta z$ versus time and to record or display their values.

What has been shown is a translation insensitive keratometer using moire deflectometry which provides a pair or moire deflectometers together with dual optical paths which process the output light beams of two laser sources having primary color wavelengths to produce separate and distinguishable moire deflectograms on each of the moire deflectometers which may be readily processed by means described herein to measure the position, x-curvature, y-curvature, and surface topography of the specular object under examination.

It should be noted that while the present invention system has been shown measuring the characteristics of the outer cornea surface, it is equally applicable to measurement of the inner cornea surface. Thus, by measurement of both cornea surfaces, the cornea thickness may be measured. When so used, the system functions as a pachymeter.

While particular embodiments of the invention have been shown and described, it will be obvious to those skilled in the art that changes and modifications may be made without departing from the invention in its broader aspects. Therefore the aim in the appended claims is to cover all such changes and modifications as fall within the true spirit and scope of the invention.

That is claimed is:

1. For use in measuring the curvature and shape of a specular object, a keratometer comprising:
    first and second moire deflectometers;
    first and second color video cameras directed to said first and second moire deflectometers respectively;
    a first source of collimated light having a first wavelength;
    a second source of collimated light having a second wavelength;
    a beam expander coupled to said first source;
    first optical transmission means coupling the output of said beam expander to the specular object such that the incident light thereon is converging and the reflected light therefrom is diverging and such that the light reflected from said specular object is received by said first and second moire deflectometers;
    second optical transmission means coupling the output of said second source to said specular object as a collimated light beam which is reflected therefrom as a diverging light beam and coupling the diverging reflected light beam to said first and second moire deflectometers as collimated light.

2. A keratometer as set forth in claim 1 wherein said first and second light sources are lasers having wavelengths corresponding to two primary colors of said color video cameras.

3. A keratometer as set forth in claim 2 wherein said first and second optical transmission means include first and second filters of said two primary colors.

4. A keratometer as set forth in claim 3 further including first and second image processors coupled to said first and second color video cameras.

5. A keratometer as set forth in claim 4 wherein said first and second optical transmission means include first and second lenses and wherein said first laser output is introduced upstream of said first lens and said second laser output is introduced downstream of said second lens.

* * * * *